(12) United States Patent
Chino et al.

(10) Patent No.: US 12,306,006 B2
(45) Date of Patent: May 20, 2025

(54) GUIDANCE SUPPORT DEVICE, GUIDANCE SUPPORT SYSTEM, AND FOOTWEAR

(71) Applicant: Ashirase, Inc., Nishitokyo (JP)

(72) Inventors: Wataru Chino, Utsunomiya (JP); Yusuke Tanaka, Tokyo (JP); Ryohei Tokuda, Utsunomiya (JP); Aya Yamahata, Tokyo (JP)

(73) Assignee: ASHIRASE, INC., Tokyo (JP)

( * ) Notice: Subject to any disclaimer, the term of this patent is extended or adjusted under 35 U.S.C. 154(b) by 127 days.

(21) Appl. No.: 17/749,829

(22) Filed: May 20, 2022

(65) Prior Publication Data

US 2022/0282986 A1 Sep. 8, 2022

Related U.S. Application Data (63) Continuation of application No. PCT/JP2020/043342, filed on Nov. 20, 2020.

(30) Foreign Application Priority Data

Nov. 25, 2019 (JP) .................................. 2019-211978

(51) Int. Cl.
- *A43B 3/44* (2022.01)
- *G01C 21/30* (2006.01)
- *G01C 21/36* (2006.01)
- *G06F 3/01* (2006.01)

(52) U.S. Cl.
CPC ............ *G01C 21/3652* (2013.01); *A43B 3/44* (2022.01); *G01C 21/30* (2013.01); *G06F 3/016* (2013.01)

(58) Field of Classification Search
CPC ...... G01C 21/3652; G01C 21/30; A43B 3/44; G06F 3/016
See application file for complete search history.

(56) References Cited

U.S. PATENT DOCUMENTS

| | | | |
|---|---|---|---|
| 9,460,557 B1 * | 10/2016 | Tran | G06T 15/205 |
| 10,721,994 B2 * | 7/2020 | Kilgore | A43B 23/0235 |
| 2008/0077283 A1 | 3/2008 | Ueyama et al. | |
| 2011/0153197 A1 | 6/2011 | Song | |

(Continued)

FOREIGN PATENT DOCUMENTS

| | | |
|---|---|---|
| EP | 3 247 093 A1 | 11/2017 |
| JP | 2008-080896 | 4/2008 |

(Continued)

OTHER PUBLICATIONS

International Search Report dated Jan. 12, 2021, Application No. PCT/JP2020/043342, 3 pages.

*Primary Examiner* — Andrea C Leggett
(74) *Attorney, Agent, or Firm* — Rankin, Hill & Clark LLP (57) ABSTRACT

In a guidance support device to be used by being inserted into footwear, a plurality of vibration generating members generate vibrations at a plurality of positions on a foot of a user who uses the guidance support device. A position acquisition part acquires a current position. A route acquisition part acquires a route from the current position to a destination. A vibration control part, on condition that a route pattern at a current position on the route fits any one of a plurality of predetermined patterns, vibrates the vibration generating members in a combination corresponding to the pattern.

8 Claims, 7 Drawing Sheets

(56) References Cited

U.S. PATENT DOCUMENTS

| | | | |
|---|---|---|---|
| 2013/0211563 A1* | 8/2013 | Ellis | A63B 69/16 700/91 |
| 2017/0325683 A1* | 11/2017 | Larson | A61B 5/1113 |
| 2017/0339524 A1 | 11/2017 | Cho et al. | |
| 2019/0289950 A1 | 9/2019 | Matsumoto et al. | |
| 2020/0359731 A1* | 11/2020 | Jun | A61B 5/0022 |

FOREIGN PATENT DOCUMENTS

| JP | 2011-062298 | 3/2011 |
|---|---|---|
| JP | 2015-075386 | 4/2015 |
| JP | 2017-015485 | 1/2017 |
| JP | 2018-163124 | 10/2018 |
| JP | 2019-168987 | 10/2019 |

\* cited by examiner

| ROUTE PATTERN ID | DESCRIPTION | VIBRATION MEMBERS | VIBRATION PATTERN |
|---|---|---|---|
| PID0001 | REACHED DESTINATION | 1, 3, 5 (BOTH FEET) | ON AND OFF (FAST) |
| PID0002 | TURN RIGHT IMMEDIATELY | 1, 3, 5 (RIGHT FOOT) | ON AND OFF (FAST) |
| PID0003 | TURN RIGHT 5 METERS AHEAD | 3, 5 (RIGHT FOOT) | ON AND OFF (SLOW) |
| ... | ... | ... | ... |
| PIDOXXX | EMERGENCY STOP | ALL (BOTH FEET) | CONTINUOUS |

| SEGMENTED REGION ID | | |
|---|---|---|
| RID000001 | | |
| DISTANCE MEASUREMENT TARGET INFORMATION | | |
| EAST LONGITUDE | NORTH LATITUDE | NAME OF OBJECRT |
| aaa | bbb | OUTER WALL OF BUILDING |
| ccc | ddd | STEPS OF PEDESTRIAN BRIDGE |
| . | . | . |
| . | . | . |
| . | . | . |
| xxx | yyy | FLOWER BED |

GUIDANCE SUPPORT DEVICE, GUIDANCE SUPPORT SYSTEM, AND FOOTWEAR

CROSS-REFERENCE TO RELATED APPLICATIONS

The present application is a continuation application of International Application number PCT/JP2020/043342, filed on Nov. 20, 2020, which claims priority under 35 U.S.C § 119(a) to Japanese Patent Application No. 2019-211978, filed on Nov. 25, 2019. The contents of this application are incorporated herein by reference in their entirety.

BACKGROUND

The present disclosure relates to a guidance support device to be used for footwear, a guidance support system including the guidance support device, and footwear, and more particularly, to a technique for providing a user with navigation to a destination.

Conventionally, various navigation systems for assisting a user who moves on foot have been proposed. For example, Japanese Unexamined Patent Application Publication No. 2017-15485 proposes an eyeglass-type navigation system that is worn on the head of a user and provides him/her with route guidance to a destination.

The above-described technique causes the eyeglass-type wearable device to display navigation information or to present the user with information by voice by having the user wear the device. However, there are cases where visually impaired users may not have a habit of wearing glasses or the like on a daily basis, and there are users who are sighted people but do not have a habit of wearing glasses or the like on a daily basis. Such users may find wearing the wearable device troublesome for navigation.

Focusing on that a user wears some kind of footwear when he/she moves on foot, the present inventors recognized the possibility of reducing the user's feeling of complexity by presenting navigation information to a foot of the user.

SUMMARY

The present disclosure focuses on this point, and its object is to provide a technique for presenting navigation information to a foot of a user.

A guidance support device according to a first aspect of the present disclosure is a guidance support device to be used by being inserted into footwear. The guidance support device includes: a plurality of vibration generating members for generating vibrations at a plurality of positions on a foot of a user who uses the guidance support device; a position acquisition part that acquires a current position; a route acquisition part that acquires a route from the current position to a destination; and a vibration control part that, on condition that a route pattern at a current position on the route fits any one of a plurality of predetermined patterns, vibrates the vibration generating members in a combination corresponding to the pattern, wherein the guidance support device is a first guidance support device used by being worn on one of the feet of the user, and the guidance support device further includes: a sensor information acquisition part that acquires first sensor information, which is information acquired by a sensor of a measurement part included in the first guidance support device, and second sensor information, which is information acquired by a sensor of a measurement part included in a second guidance support device used by being worn on the other foot of the user; a failure detection part that analyzes a difference between the first sensor information and the second sensor information and detects a failure of at least one of the measurement part included in the first guidance support device or the measurement part included in the second guidance support device; and a failure notification part that notifies the second guidance support device that the failure has been detected.

A second aspect of the present disclosure is footwear. Footwear which is a pair of footwear to be worn respectively on the feet of a user, the footwear respectively includes: a plurality of vibration generating members for generating vibrations at a plurality of positions on one of the feet of the user; a position acquisition part that acquires a current position; a route acquisition part that acquires a route from the current position to a destination; a vibration control part that, on condition that a route pattern included in the route at the current position fits any one of a plurality of predetermined patterns, vibrates the vibration generating members in a combination corresponding to the pattern; a sensor information acquisition part that acquires first sensor information, which is information acquired by a sensor of a measurement part included in the footwear used by being worn on one of the feet of the user, and second sensor information, which is information acquired by a sensor of a measurement part included in footwear used by being worn on the other foot of the user; a failure detection part that analyzes a difference between the first sensor information and the second sensor information and detects a failure of at least one of the measurement part included in the footwear worn on one of the feet of the user or the measurement part included in the footwear worn on the other foot of the user; and a failure notification part that notifies the footwear worn on the other foot of the user that the failure has been detected.

It should be noted that any combination of the above-described constituent elements, and an aspect obtained by converting the expression of the present disclosure among methods, devices, systems, computer programs, data structures, recording media, and the like are also effective as an aspect of the present disclosure.

DETAILED DESCRIPTION OF THE INVENTION

Hereinafter, the present disclosure will be described through exemplary embodiments, but the following exemplary embodiments do not limit the invention according to the claims, and not all of the combinations of features described in the exemplary embodiments are necessarily essential to the solution means of the invention.

Outline of the Embodiment

Figure 1A:
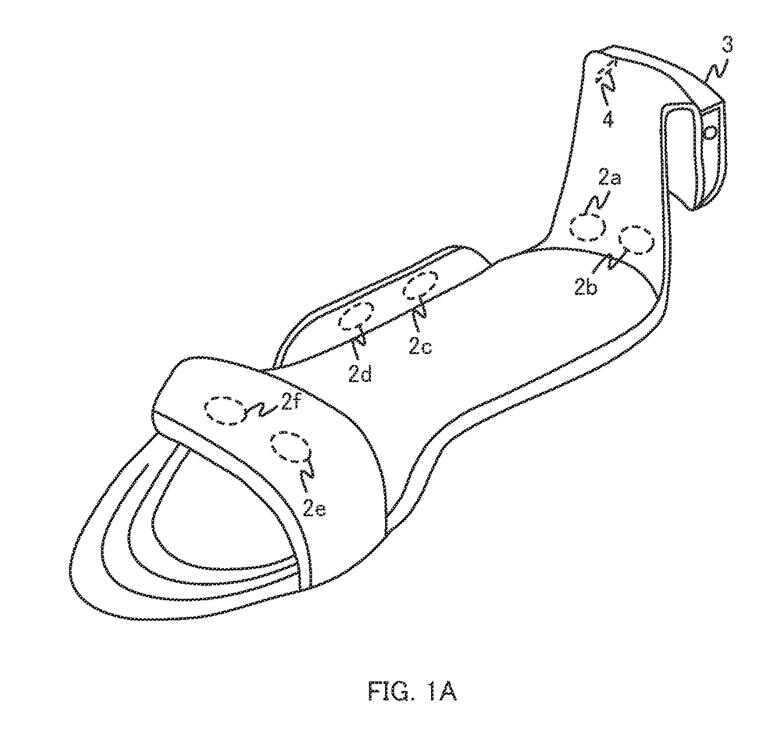
FIGS. 1A and 1B are each a schematic diagram showing an outline of a navigation system according to an embodiment.
Figure 1B:
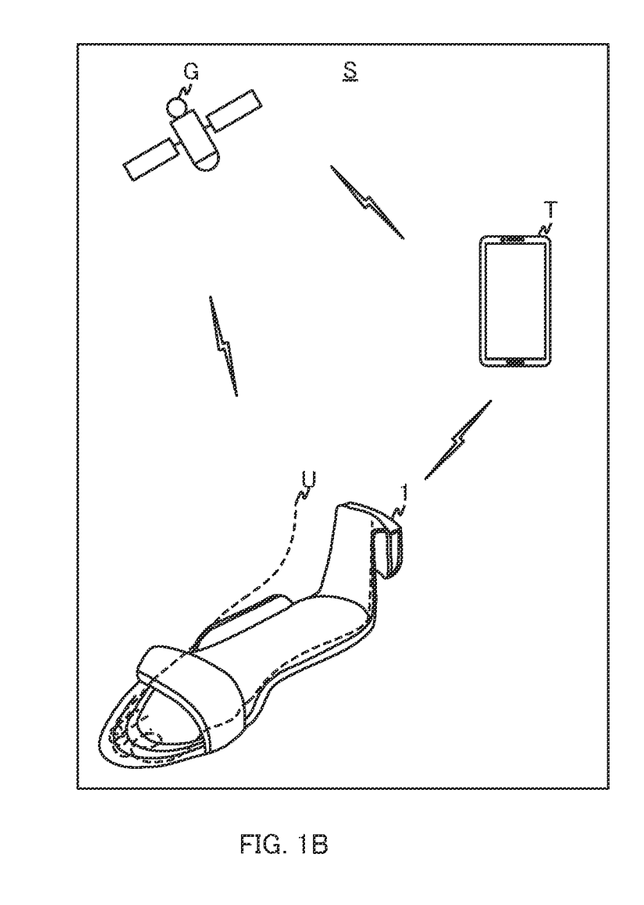

FIGS. 1A and 1B are each a schematic diagram showing an outline of a navigation system S according to the embodiment. Specifically, FIG. 1A is a schematic diagram showing the overall configuration of the navigation system S according to the embodiment, and FIG. 1B is a schematic diagram showing the overall configuration of a guidance support device 1 according to the embodiment. An example of the guidance support device 1 according to the embodiment shown in FIG. 1B takes the shape of an insole. Therefore, hereinafter, the guidance support device 1 is also referred to as an "insole 1".

As shown in FIG. 1A, the navigation system S according to the embodiment includes the insole 1 (only for the right foot, while the one for the left foot is not shown) for use in footwear (not shown) such as shoes, and a mobile terminal T that can communicate with the insole 1. The insole 1 includes a communication part for receiving navigation signals from a navigation satellite G and for wirelessly communicating with the mobile terminal T. The mobile terminal T is a known smartphone, for example, and can receive the navigation signals from the navigation satellite G in a similar manner as with the insole 1.

The insole 1 functions as a so-called shoe insole, and is used by being inserted in footwear. In FIG. 1A, a foot of a user U wearing the footwear in which the insole 1 is inserted is indicated by a broken line. In the example shown in FIGS. 1A and 1B, the insole 1 is formed such that when the user U wears the footwear in which the insole 1 is inserted it contacts the sole of the foot, the instep of the foot, the heel, and the like of the user.

The insole 1 includes a plurality of vibration generating members 2 for generating vibrations at a plurality of positions on a foot of the user U who uses the insole 1. FIG. 1B shows an example in which the insole 1 includes six vibration generating members 2 from a first vibration generating member 2a to a sixth vibration generating member 2f, but the number of vibration generating members 2 is not limited to six. The vibration generating member 2 may be any member as long as it can generate a vibration in the epidermis of the foot of the user U, and can be realized by using a motor or electrical muscle stimulation (EMS), for example.

The insole 1 also includes a processing apparatus 3 for controlling movement of each vibration generating member 2. The processing apparatus 3 is a microcomputer mounted on a flexible substrate or the like and can generate or stop the vibration in the epidermis of the user U using the vibration generating members 2, for example.

The insole 1 according to the embodiment presents a direction that the user U should move towards by generating the vibration in the epidermis of the foot of the user U using the vibration generating members 2. When the user U inputs a destination to the insole 1 via the mobile terminal T, the insole 1 acquires a route from a current position of the user U (that is, a current position of the insole 1) to the destination, and starts navigation. The insole 1 causes the vibration generating members 2 to generate vibrations at a timing when the user U traveling on the acquired route needs to make a motion such as turning to the right or going up steps.

At this time, the insole 1 changes a pattern of vibrations to be generated by the vibration generating members 2 according to a pattern of motion the user U should make. For example, when the user U needs to turn right, the insole 1 vibrates only the vibration generating members 2 disposed on the right side of the foot of the user U. Alternatively, when the user U needs to go up the steps, the insole 1 vibrates only the vibration generating members 2 disposed on the instep side of the foot of the user U. In this way, the insole 1 can present navigation information to the foot of the user U by changing the pattern of vibrations to be generated by the plurality of vibration generating members 2. As shown in FIG. 1B, the insole 1 also has a distance measuring part 4 provided such that it is positioned at the heel of the user U, and details thereof will be described later.

Functional Configuration of the Insole 1 According to the Embodiment

Figure 2:
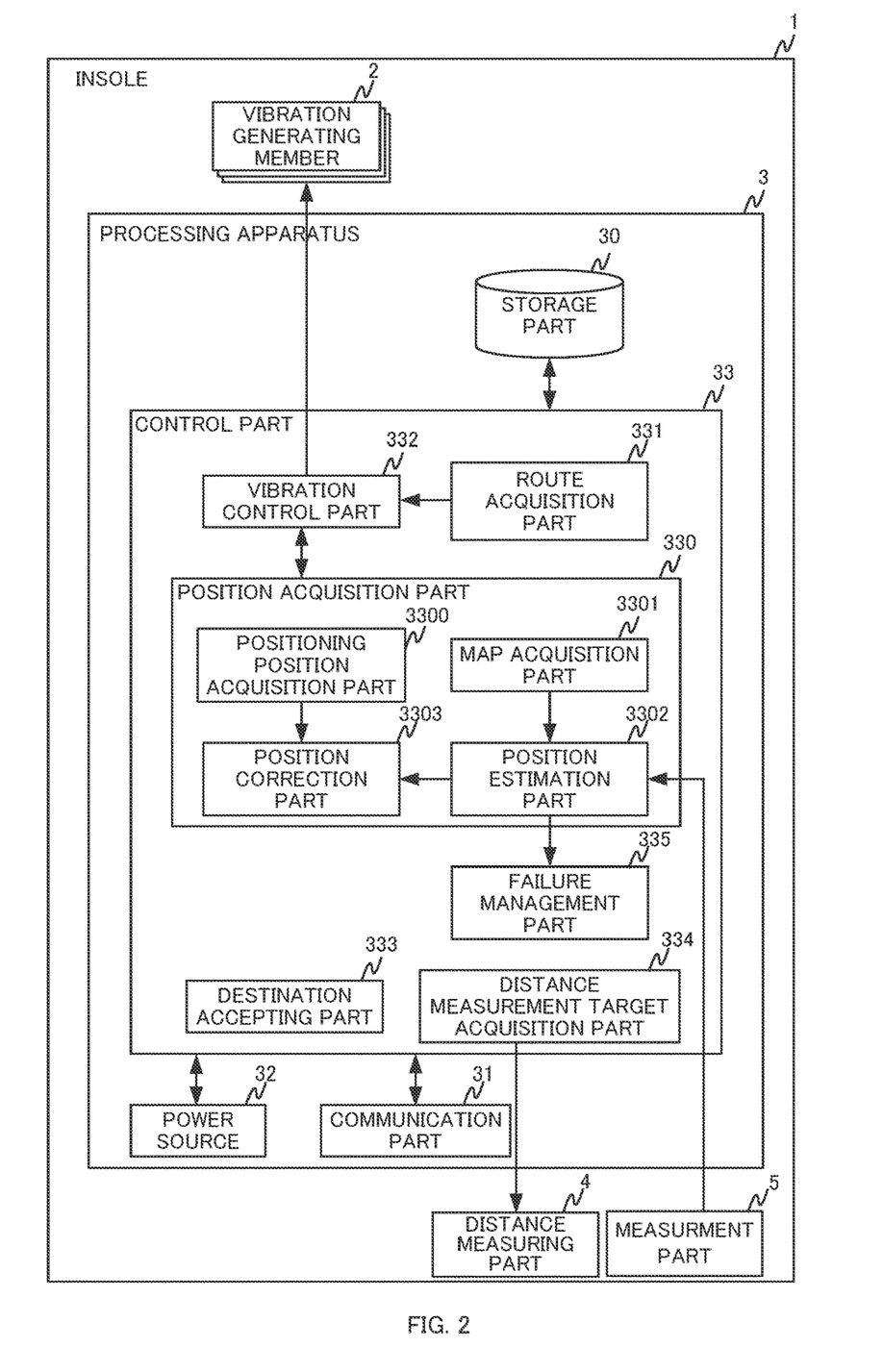
FIG. 2 is a schematic diagram showing a functional configuration of an insole according to the embodiment.

FIG. 2 is a schematic diagram showing a functional configuration of the insole 1 according to the embodiment. The insole 1 includes the plurality of vibration generating members 2, the processing apparatus 3, the distance measuring part 4, and a measurement part 5. The processing apparatus 3 includes a storage part 30, a communication part 31, a power source 32, and a control part 33. In FIG. 2, arrows indicate main data flows, and there may be data flows not shown in FIG. 2. In FIG. 2, each functional block indicates a configuration of a function unit, not a configuration of a hardware (device) unit. Therefore, the functional blocks shown in FIG. 2 may be implemented in a single device, or may be implemented separately in a plurality of devices.

The storage part 30 is a storage device that stores (i) a read only memory (ROM) which stores a basic input output system (BIOS) for a computer, and the like that realize the processing apparatus 3, (ii) a random access memory (RAM) which is a work area of the processing apparatus 3, (iii) an operating system (OS) and application programs, and (iv) various types of information to be referenced when executing the application programs.

The communication part 31 is an interface through which the processing apparatus 3 exchanges signals with an external device. Specifically, the communication part 31 can be realized by using a known wireless communication module such as Wi-Fi (registered trademark) or Bluetooth (registered trademark) and a global navigation satellite system (GNSS) receiving module. Hereinafter, when the processing apparatus 3 according to the embodiment communicates with an external device, the description thereof will be omitted assuming that communication is performed via the communication part 31.

The power source 32 supplies electric power for driving the processing apparatus 3. The power source 32 can be realized by using a known battery such as a lithium ion secondary battery, and also includes a mechanism for charging in a non-contact manner.

The control part 33 is a processor such as a central processing unit (CPU) or the like of the processing apparatus 3, and functions as a position acquisition part 330, a route acquisition part 331, a vibration control part 332, a destination accepting part 333, a distance measurement target acquisition part 334, and a failure management part 335 by executing programs stored in the storage part 30. Each part of the processing apparatus 3 may be realized by hardware such as an application specific integrated circuit (ASIC).

The position acquisition part 330 acquires a current position of the insole 1. The route acquisition part 331 acquires a route from the current position of the insole 1 to a destination. The route acquisition part 331 may acquire a route generated by the mobile terminal T by receiving the route from the mobile terminal T. When the storage part 30 stores map information, the route acquisition part 331 may calculate and acquire the route from the current position of the insole 1 to the destination on the basis of the map information read from the storage part 30.

The destination accepting part 333 accepts setting of the destination from the user U. More specifically, the destination accepting part 333 accepts the destination by receiving the destination set in the mobile terminal T by the user U. When the destination accepting part 333 includes a voice recognition function, the destination accepting part 333 may directly accept setting of the destination from the user U by voice.

The vibration control part 332, on condition that a route pattern at a current position on the route fits any one of a plurality of predetermined patterns, vibrates the vibration generating members 2 in a combination corresponding to said pattern.

Here, the "predetermined plurality of patterns" are patterns on the route which should cause some sort of change in the motion of the user U in order to guide the user U to the destination. Examples of the plurality of predetermined patterns include a pattern that prompts the user U to turn left on the route, a pattern that prompts the user U to go up using an elevator, and the like.

Figure 3:
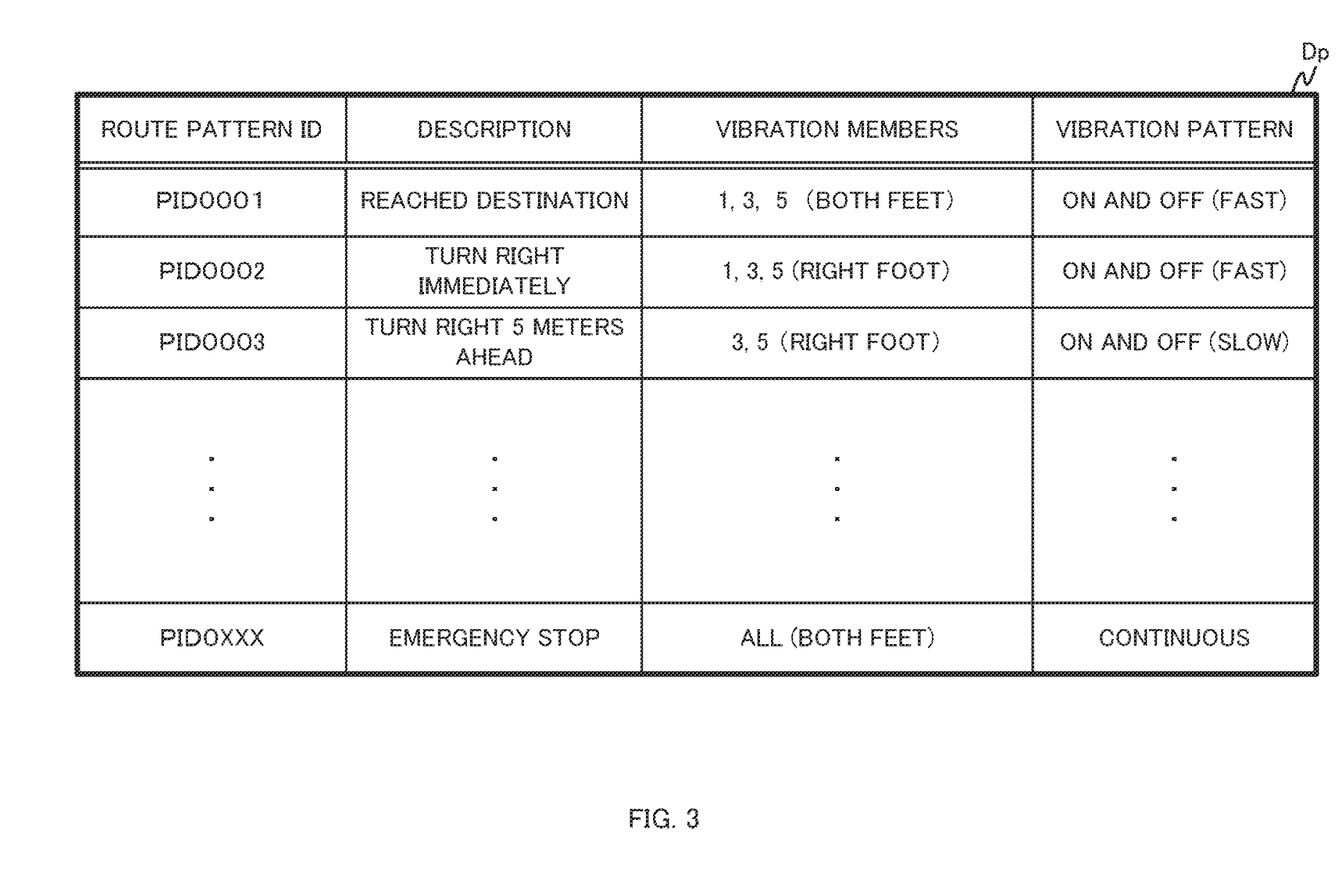
FIG. 3 is a schematic diagram showing a data structure of a pattern database which a vibration control part according to the embodiment references.

FIG. 3 is a schematic diagram showing a data structure of a pattern database Dp which the vibration control part 332 according to the embodiment references. The pattern database Dp is stored in the storage part 30 and managed by the vibration control part 332. As shown in FIG. 3, in the pattern database Dp, a pattern identifier is assigned to each pattern on the route which should cause some sort of change in the motion of the user U. For example, a route pattern whose route pattern identifier is PID0001 is "reached destination," and a route pattern whose route pattern identifier is PID0002 is "turn right immediately".

The six vibration generating members 2 of the insole 1 are also assigned serial numbers from 1 to 6. For example, "1" is assigned to the first vibration generating member 2a, "2" is assigned to the second vibration generating member 2b, and so forth.

As shown in FIG. 3, in the pattern database Dp, which of the vibration generating members 2 should generate a vibration and how to generate a vibration are determined for each route pattern identifier. For example, the pattern whose route pattern identifier is PID0001 is a pattern that informs the user U of arrival at a destination, and is a pattern where the first vibration generating member 2a, the third vibration generating member 2c, and the fifth vibration generating member 2e intermittently generate vibrations. Also, the pattern whose route pattern identifier is PID0XXX is a pattern that informs the user U that he/she should make an emergency stop for some reason and is a pattern where all the vibration generating members 2 continuously generate vibrations.

As described above, the insole 1 according to the embodiment can present the navigation information to the foot of the user U by changing the pattern of vibrations to be generated in the vibration generating members 2 according to the route pattern at the current position of the insole 1.

[Details of Position Information Acquisition]

In the insole 1 according to the embodiment, since the pattern of vibrations to be generated by the vibration generating members 2 is changed according to the route pattern at the current position of the insole 1, accuracy of the current position of the insole 1 (that is, information about the current position acquired by the position acquisition part 330) is important. Hereinafter, an acquisition process of a current position by the position acquisition part 330 according to the embodiment will be described.

As shown in FIG. 2, the position acquisition part 330 includes a positioning position acquisition part 3300, a map acquisition part 3301, a position estimation part 3302, and a position correction part 3303. The positioning position acquisition part 3300 acquires a positioning position on the basis of the navigation signals received from the navigation satellite G. In general, it is known that a positioning position which the positioning position acquisition part 3300 calculates on the basis of the navigation signals includes an error due to factors such as the type of navigation signals and the radio wave condition. The degree of this error varies depending on the type of the navigation signals transmitted by the navigation satellite G, the presence or absence of a structure that reflects the navigation signals, or the like, and if the degree of error is large, it may be about several meters to several tens of meters. For this reason, if the insole 1 relies only on the positioning position acquired by the positioning position acquisition part 3300, there may be a case where the insole 1 cannot provide highly accurate navigation information to the user U.

Therefore, the position acquisition part 330 according to the embodiment corrects the positioning position acquired by the positioning position acquisition part 3300 on the basis of information obtained from a known acceleration sensor, a known gyro sensor, a known electronic compass (not shown), or the like. Specifically, the map acquisition part 3301 first acquires map information including a route. Here, when the storage part 30 stores the map information, the map acquisition part 3301 reads and acquires the map information from the storage part 30. Alternatively, the map acquisition part 3301 may receive and acquire map information from the mobile terminal T.

Figure 4:
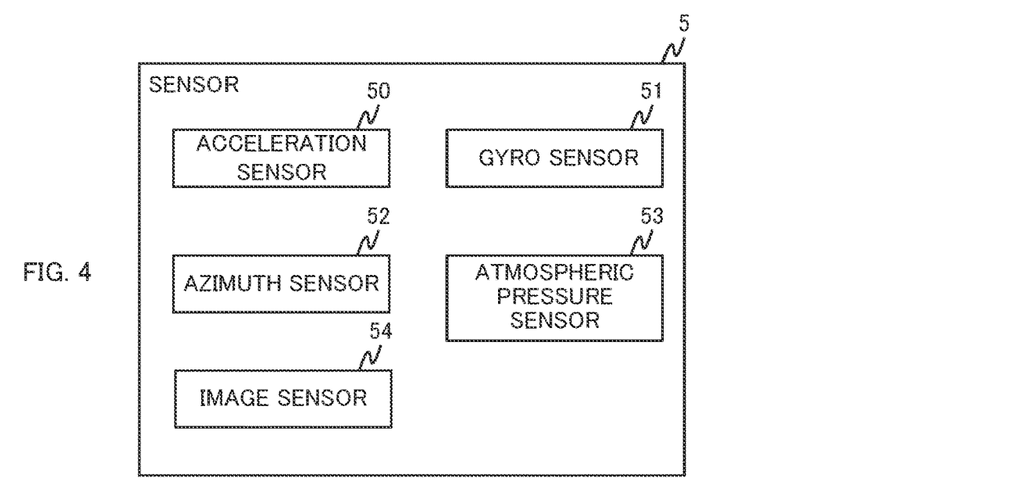
FIG. 4 is a diagram schematically showing an example of various types of sensors included in a measurement part according to the embodiment.

Next, the position estimation part 3302 estimates a position of the insole 1 independently of the positioning position acquisition part 3300, on the basis of information collected by the measurement part 5. FIG. 4 is a diagram schematically showing an example of various types of sensors included in the measurement part 5 according to the embodiment. As shown in FIG. 4, the measurement part 5 includes all of an acceleration sensor 50, a gyro sensor 51, an azimuth sensor 52, an atmospheric pressure sensor 53, and an image sensor 54, or at least one of the acceleration sensor 50, the gyro sensor 51, the azimuth sensor 52, the atmospheric pressure sensor 53, or an image sensor 54. In general, unlike information based on the navigation signals, the position estimation part 3302 cannot estimate absolute position information of the insole 1 from the information based on the acceleration sensor 50, the gyro sensor 51, the azimuth sensor 52, or the like. Therefore, the position estimation part 3302 estimates a relative position based on a base point position that is in the map information acquired by the map acquisition part 3301. The position estimation part 3302 improves estimation accuracy of the relative position by estimating an integral value, which is an output of the gyro sensor 51 or the like, by using a known estimation technique such as a Kalman filter. Since it is a known technology, detailed explanation is omitted. The relative position based on the base point position is also the absolute position information because the base point position that exists on a map is absolute position information.

The position correction part 3303 calculates the current position of the insole 1 by correcting the positioning position using the relative position estimated by the position estimation part 3302.

Figure 5:
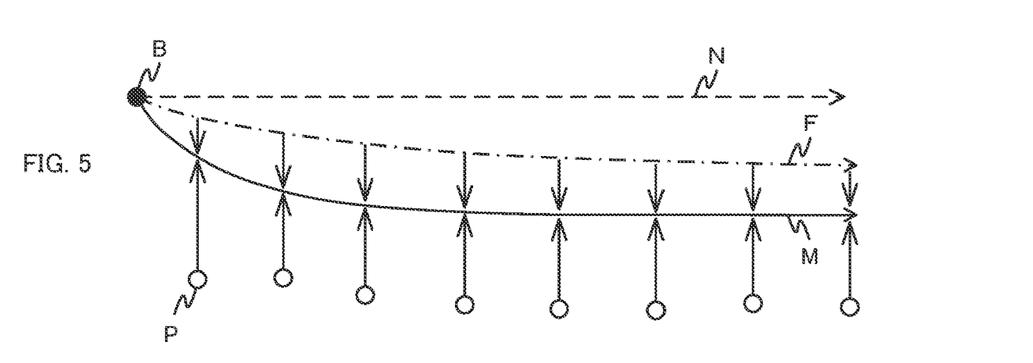
FIG. 5 is a diagram illustrating a position correcting process performed by a position estimation part according to the embodiment.

FIG. 5 is a diagram illustrating a position correcting process performed by the position correction part 3303 according to the embodiment. In FIG. 5, a point denoted by a letter B is a base point position B that exists on the map. A broken line denoted by a letter N is a guiding direction N indicating a direction from the base point position B toward the destination. A dashed line denoted by a letter F is a trajectory F of the relative position acquired by the position estimation part 3302 based on the base point position B.

A white circle denoted by a letter P indicates the positioning position acquired by the positioning position acquisition part 3300 on the basis of the navigation signals received from the navigation satellite G. For simplicity, not all white circles in FIG. 5 are denoted by letters P, but all white circles in FIG. 5 indicate the positioning positions acquired by the positioning position acquisition part 3300.

A solid line denoted by a letter M indicates a corrected positioning position M which is the positioning position corrected by the position correction part 3303 by using the relative position estimated by the position estimation part 3302. As shown in FIG. 5, the position correction part 3303 corrects the positioning position so that the positioning position acquired by the positioning position acquisition part 3300 is brought close to the relative position estimated by the position estimation part 3302. In this manner, the position correction part 3303 can improve estimation accuracy of the current position of the insole 1 by referencing the two pieces of position information which are independently estimated on the basis of different pieces of information.

[Update of the Base Point Position]

As described above, the position estimation part 3302 estimates the relative position of the insole 1 based on the base point position B that exists on the map, but generally, an estimation error tends to increase as the insole 1 moves away from the base point position B. Therefore, the insole 1 according to the embodiment updates the base point position B under certain conditions.

In order to realize this, the insole 1 includes a distance measuring part 4 that measures a distance to an object around the footwear in which the insole 1 is used. The distance measuring part 4 can be realized by using a known infrared distance measurement sensor, a known sonic distance measurement sensor, a known distance image sensor, or the like, for example.

As shown in FIGS. 1A and 1B, the distance measuring part 4 is provided such that it is positioned against the heel of the user U when the user U wears the footwear using the insole 1. Since this makes the position of the distance measuring part 4 higher than the ground, it is possible to prevent a reduction in the accuracy of the distance measurement due to an obstacle such as a small stone on the ground where the user U walks.

The position estimation part 3302 updates the base point position B on the basis of information concerning a distance measurement target included in the map information and the distance measured by the distance measuring part. Here, the "distance measurement target" is an object referenced by the position estimation part 3302 in order to determine whether to update the base point position B, and varies by the region in which a route to be presented to the user U is included. For example, when the user U walks in urban areas, it is assumed that he/she travels on a sidewalk. Therefore, a structure such as an outer wall of a building that exists around the sidewalk may be the distance measurement target. When the user U walks in mountain areas, trees, rocks, road signs, or the like that are near a mountain trail may be the distance measurement targets.

Figure 6:
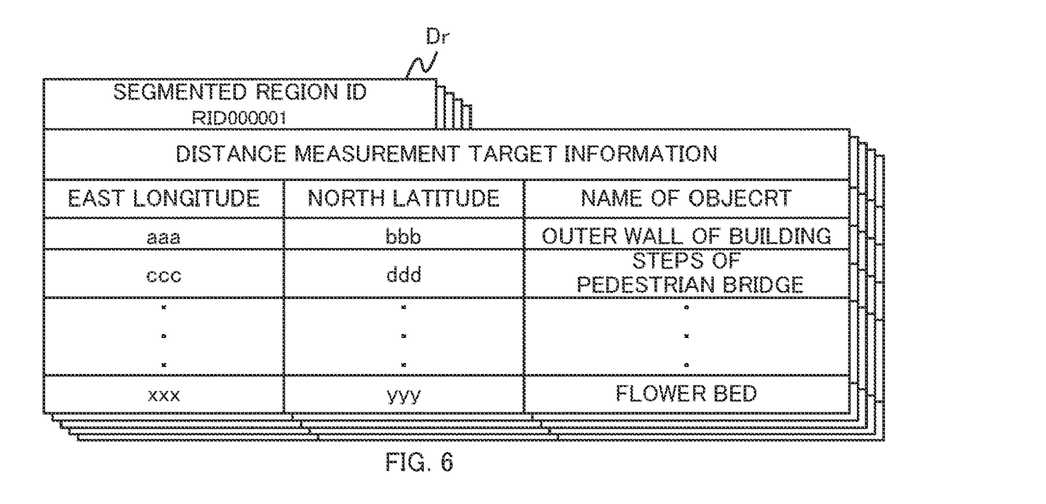
FIG. 6 is a schematic diagram showing a data structure of a distance measurement target database according to the embodiment.

FIG. 6 is a schematic diagram showing a data structure of a distance measurement target database Dr according to the embodiment. The distance measurement target database Dr is stored in the storage part 30 and managed by the position estimation part 3302. As shown in FIG. 6, the distance measurement target database Dr manages the distance measurement targets by dividing map information into a plurality of segmented regions and assigning a segmented region identifier to each segmented region. FIG. 6 exemplifies information concerning a distance measurement target in a segmented region whose segmented region identifier is RID 000001. As shown in FIG. 6, the distance measurement target database Dr stores the information concerning the distance measurement target determined for each segmented region in association with the segmented region.

As described above, objects that can be the distance measurement targets differ according to the type of land, such as urban areas, mountainous areas, forests, sand beaches, hot-spring districts, and prairies. Therefore, the "segmented region" is determined in advance in consideration of the type of land or the like, and is registered in the map information acquired by the map acquisition part 3301. FIG. 6 shows examples of the distance measurement targets when the segmented region is an urban area. Therefore, objects such as an outer wall of a building, steps of a pedestrian bridge, a flower bed, and the like that exist in the urban area are distance measurement targets.

The position estimation part 3302 determines a deviation between (i) a distance on a map to the distance measurement target that exists on the route presented to the user U and (ii) an actual distance measured by the distance measuring part 4. On condition that the deviation is equal to or greater than a predetermined length, the position estimation part 3302 sets an object measured by the distance measuring part 4 at that time as a new base point position B.

Here, the "predetermined length" is an "update determination reference length" which is referenced by the position estimation part 3302 in order to determine whether to update the base point position B. When the deviation between the distance on the map to the distance measurement target and the actual distance measured by the distance measuring part 4 is within the predetermined length, the position estimation part 3302 relies on the distance measured by the distance measuring part 4 and corrects position coordinates.

Since the position estimation part 3302 updates the base point position B on the basis of the information concerning the distance measurement target and the distance measured by the distance measuring part 4 in this manner, the position estimation part 3302 can maintain the estimation accuracy of the relative position.

[Instruction to Stop]

The position estimation part 3302 determines whether the deviation between (i) the distance on the map from the current position to the distance measurement target and (ii) the distance measured by the distance measuring part 4 is within a predetermined threshold distance. Here, the "predetermined threshold distance" is a "reference distance for determining a distance measuring operation" which is referenced by the position estimation part 3302 in order to determine whether a distance measurement by the distance measuring part 4 is operating normally. The greater the deviation between (i) the distance on the map from the current position to the distance measurement target and (ii) the distance measured by the distance measuring part 4, the higher the probability that the distance measurement by the distance measuring part 4 has failed. Since the distance measurement by the distance measuring part 4 is used for correcting the positioning position by the positioning position acquisition part 3300, if the distance measurement by the distance measuring part 4 fails, accuracy of the navigation information presented by the insole 1 may decrease. Also, when the distance measuring part 4 cannot measure the distance to the distance measurement target even though the distance measurement target is on the map (that is, when the distance measuring part 4 cannot detect a distance measurement target), it is difficult to maintain the accuracy of the navigation information presented by the insole 1.

Therefore, when the deviation between (i) the distance on the map from the current position to the distance measurement target and (ii) the distance measured by the distance measuring part 4 exceeds the predetermined threshold distance or when the distance measuring part 4 cannot detect a distance measurement target, the vibration control part 332 vibrates the vibration generating members 2 in a combination determined to prompt the user U to stop. Specifically, in the pattern database Dp shown in FIG. 3, the vibration control part 332 vibrates the vibration generating members 2 in a pattern whose route pattern identifier is PID0XXX. By doing this, the insole 1 can avoid presenting navigation information with poor accuracy to the user U.

When the distance measurement by the distance measuring part 4 fails, the mobile terminal T may utter a voice to communicate about the failure, may display a message on a display screen of the mobile terminal T, or may inform the user U of the failure by a vibration function included in the mobile terminal T.

[Detection of a Failure]

The above has been described on the premise that the position estimation part 3302 operates normally. Since the position estimation part 3302 estimates the position on the basis of the information collected by the measurement part 5, estimation accuracy depends on a measurement result of the measurement part 5. For example, when a failure or the like occurs in the measurement part 5, accuracy of the position estimation by the position estimation part 3302 may affect the guidance support of the user U. There are some cases where the failure can be detected independently from characteristic abnormality of each sensor included in the measurement part 5, but on the other hand, there may be a failure state in which it is difficult for the position estimation part 3302 to independently detect a failure of the sensor. This is because the position estimation part 3302 does not have a reference for determining whether the information collected by the measurement part 5 is correct.

Therefore, the failure management part 335 detects a failure of each sensor included in the measurement part 5 on the basis of a difference between (i) information collected by the measurement part 5 (hereinafter, this may be referred to as a "first measurement part") included in an insole 1 for the right foot (hereinafter, this may be referred to as a "first guidance support device") of the user U and (ii) information collected by the measurement part 5 (hereinafter, this may be referred to as a "second measurement part") included in an insole 1 for the left foot (hereinafter, this may be referred to as a "second guidance support device") of the user U. When neither the first measurement part nor the second measurement part has failed, measurement values of the first measurement part and the second measurement part should show similar values. On the other hand, when at least one of the first measurement part or the second measurement part fails, a significant difference should appear between their measurement values since the first measurement part and the second measurement part are independent of each other. Therefore, the failure management part 335 analyzes the difference between the information collected by the first measurement part and the information collected by the second measurement part, thereby detecting whether or not any of the measurement parts 5 has failed.

Figure 7:
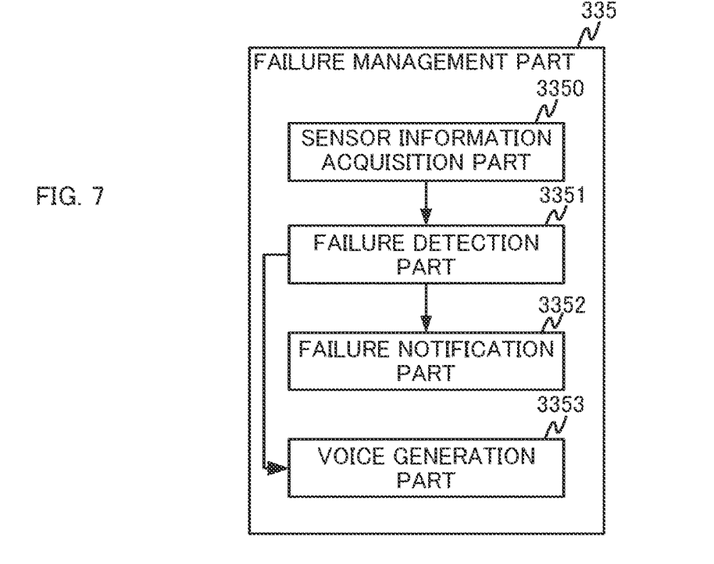
FIG. 7 is a schematic diagram showing a functional configuration of a failure management part according to the embodiment.

FIG. 7 is a schematic diagram showing a functional configuration of the failure management part 335 according to the embodiment. The failure management part 335 includes a sensor information acquisition part 3350, a failure detection part 3351, a failure notification part 3352, and a voice generation part 3353. FIG. 7 illustrates the failure management part 335 included in the first guidance support device, and the failure management part 335 included in the second guidance support device also has the same functional configuration.

The sensor information acquisition part 3350 acquires (i) first sensor information which is information acquired by various sensors of the first measurement part and (ii) second sensor information which is information acquired by various sensors of the second measurement part.

The failure detection part 3351 analyzes a difference between the first sensor information and the second sensor information to detect a failure of at least one of the first measurement part or the second measurement part. The failure notification part 3352 notifies the second guidance support device that the failure has been detected.

For example, the acceleration sensor 50, the gyro sensor 51, the azimuth sensor 52, or the atmospheric pressure sensor 53 converts a physical quantity of the outside world into numerals and detects them. Since the first guidance support device and the second guidance support device are respectively worn on the right foot and the left foot of the same user U, the numerical values detected by each sensor have approximately the same values when each sensor operates normally, and variations (for example, variance values) thereof should be within a predetermined range. This is because when the user U is walking, the left foot and the right foot will have similar accelerations, and the left foot and the right foot cannot move in different directions. In addition, since the altitude at which the right foot and the left foot exist is the same, it is considered that atmospheric pressure around them is the same.

Further, images captured by the image sensor 54 of the first guidance support device and the image sensor 54 of the second guidance support device are also approximately the same. Therefore, an average luminance, hue distribution, and dispersion of luminance of the images or various types of statistical quantities related to an image such as the histogram shape or the like of pixel values of a red pixel, a green pixel, and a blue pixel captured by the respective image sensors 54 should have the same values, for example. When the difference between the first sensor information and the second sensor information is significant, the failure detection part 801 can estimate that at least one of the first measurement part or the second measurement part has failed.

In response to a detection of the failure by the failure detection part 3351, the failure notification part 3352 sends information to a pre-registered external device via the mobile terminal T that can communicate with the first guidance support device. Here, "a pre-registered notification destination" is a telephone number, an email address, a web service, or the like set in advance by the user U, for example. By registering a telephone number or email address of a family member's mobile phone or contact information or the like of a call center of a service provider providing the guidance support using the guidance support device 1, for example, the user U can receive services such as an arrangement for a taxi and voice guidance instructions as needed, since the guidance support device 1 can quickly notify a person other than the user U when the measurement part 5 of the guidance support device 1 fails for some reason.

When the failure notification part 3352 detects a failure, the vibration control part 332 of the first guidance support device and the vibration control part 332 of the second guidance support device respectively continue to vibrate the vibration generating members 2 for a predetermined time (e.g., 10 seconds, time defined for the user U to recognize an instruction to stop) in the combination determined to prompt the user U to stop. By doing this, the guidance support device 1 can prevent the guidance support of the user U from being performed in a state where the failure of the measurement part 5 is suspected. Thereafter, the vibration control part 332 of the first guidance support device and the vibration control part 332 of the second guidance support device respectively stop the vibrations of the vibration generating members 2. By doing this, the guidance support device 1 can prevent the vibration generating members 2 from continuing to vibrate even after the user U stopped.

When the failure detection part 3351 detects the failure of at least one of the first measurement part or the second measurement part, the voice generation part 3353 causes a speaker (not shown) to generate a warning sound that notifies of the failure. By doing this, the voice generation part 3353 can quickly notify the user U that the failure has occurred, even if the user U is visually impaired.

<Process Flow of a Vibration Generation Control Process Executed by the Insole 1>

Figure 8:
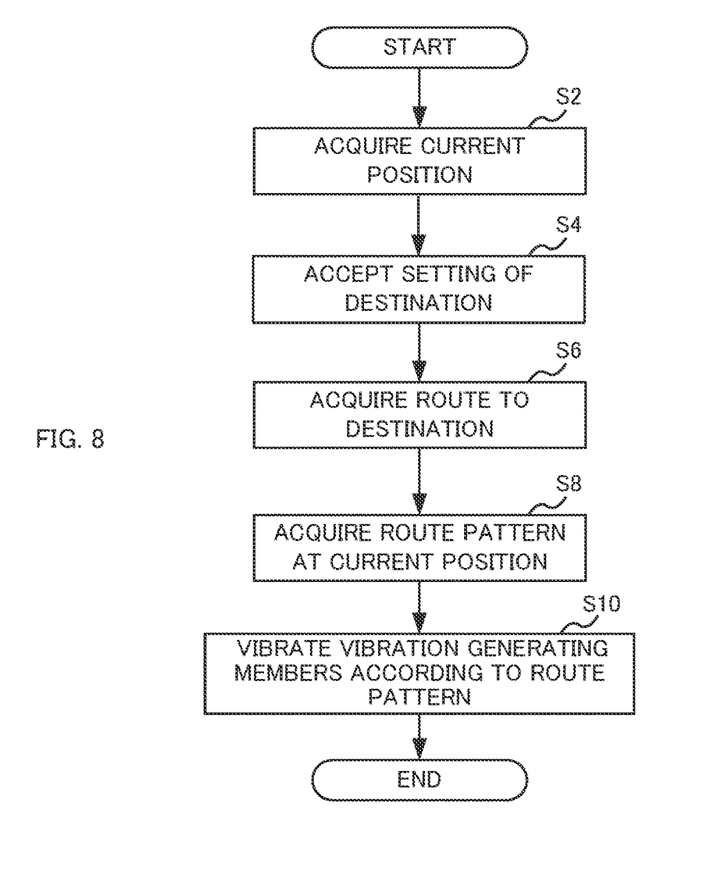
FIG. 8 is a flowchart illustrating a vibration generation control process executed by the insole according to the embodiment.

FIG. 8 is a flowchart illustrating a vibration generation control process executed by the insole 1 according to the embodiment. The process in this flowchart starts when the insole 1 starts navigation, for example.

The position acquisition part 330 acquires a current position of the insole 1 (S2). The destination accepting part 333 accepts setting of a destination from the user U (S4). The route acquisition part 331 acquires a route to the destination accepted from the user U (S6).

The vibration control part 332 acquires a route pattern at the current position on the route acquired by the route acquisition part 331 (S8). The vibration control part 332 causes the vibration generating members 2 to generate vibrations in a pattern according to the acquired route pattern (S10). By repeating the above, the insole 1 can present navigation information to the foot of the user U.

Effect Achieved by the Insole 1 According to the Embodiment

As described above, according to the insole 1 of the embodiment, the navigation information can be presented to the foot of the user U. Since the insole 1 is used for footwear which the user U always wears when he/she walks, the user U is freed from a hassle of wearing a device for navigation each time he/she goes out for a walk. Further, by causing the vibration generating members 2 to generate vibrations in the epidermis of the user U, the insole 1 presents the user U with the navigation information via the user U's sense of touch. Therefore, the insole 1 can present the navigation information not only to sighted people but also to those with visual impairments.

The present disclosure is explained based on the exemplary embodiments. The technical scope of the present disclosure is not limited to the scope explained in the above embodiments and it is possible to make various changes and modifications within the scope of the disclosure. For example, all or part of the apparatus can be configured with any unit which is functionally or physically dispersed or integrated. Further, new exemplary embodiments generated by arbitrary combinations of them are included in the exemplary embodiments. Further, effects of the new exemplary embodiments brought by the combinations also have the effects of the original exemplary embodiments. Hereinafter, such variation examples will be described.

Variation Example 1

Cases where the insole 1 includes the vibration generating members 2, the processing apparatus 3, and the distance measuring part 4 were explained above. Alternatively, the footwear itself may include at least a part or all of the vibration generating members 2, the processing apparatus 3, and the distance measuring part 4.

Variation Example 2

Cases where the position acquisition part 330 acquires the current position on the basis of the navigation signals received from the navigation satellite G were explained above. Alternatively or additionally, the position acquisition part 330 may acquire the current position by receiving signals from a beacon installed in a building or infrastructure. In this way, the insole 1 can present the user U with the navigation information even in an environment where it is difficult to receive the navigation signals from the navigation satellite G, such as in an underground walkway or inside a building.

Variation Example 3

Cases where the distance measuring part 4 measures the distance between the distance measurement target and the insole 1 were explained above. Here, since the distance measuring part 4 is provided in the insole 1 used for footwear of the user U, the distance measuring part 4 moves as he/she walks. Therefore, accuracy of the distance measurement may be reduced due to a movement of the distance measuring part 4 in a case where the distance measuring part 4 is realized by a camera, for example.

Therefore, the insole 1 may include an acceleration measurement unit (not shown) for measuring acceleration of the insole 1. The distance measuring part 4 measures a distance to an object around the footwear on condition that the acceleration of the insole 1 is less than a predetermined threshold. Here, the "predetermined threshold" is a distance measurement accuracy holding threshold determined in order to ensure distance measurement accuracy of the distance measuring part 4. Generally, when the user U walks, acceleration of one of a pair of footwear in contact with the ground is 0 or a value close to 0, although for an extremely short period of time. The predetermined threshold may be set by measuring a value of acceleration when the one of the pair of footwear is in contact with the ground by conducting an experiment. In this way, measurement accuracy of the distance between the distance measurement target and the insole 1 measured by the distance measuring part 4 can be stabilized.

Variation Example 4

Cases where the vibration control part 332 vibrates the vibration generating members 2 in the combination determined to prompt the user U to stop when the distance measurement by the distance measuring part 4 is not operating normally were explained above. Here, when the distance measuring part 4 includes a plurality of different sensors (for example, the sonic distance measurement sensor and the distance image sensor), the insole 1 may resume navigation, on condition that distance measurement by a distance measurement sensor different from the sensor whose distance measurement has failed is successful. For example, even when distance measurement by the sonic distance measurement sensor failed, the insole 1 starts navigation if a deviation between (i) the distance on the map from the current position to the distance measurement target and (ii) a distance measured by the distance image sensor is less than the threshold distance. In this way, the insole 1 is effective in that a state where navigation is stopped can be quickly resolved.

Variation Example 5

Cases where the distance measurement target database Dr stores the information concerning the distance measurement target for each of the plurality of segmented regions set in the map information were explained above. Here, the mobile terminal T may download information concerning a distance measurement target in a segmented region not stored in the storage part 30 from a specific server via a communication network such as the Internet. In this way, even when data capacity of the storage part 30 is small, the user U who uses the insole 1 can acquire the information concerning the distance measurement target in a segmented region where he/she wants to receive navigation information on demand.

Variation Example 6

Cases where the guidance support device 1 takes the shape of the insole of footwear were mainly explained above. However, the guidance support device 1 is not limited to the shape of the insole, and may take another shape. Hereinafter, a case where the guidance support device 1 takes a shape other than the insole will be described. Hereinafter, regarding a guidance support device 1 according to Variation Example 6, the same functions as those of the insole 1 according to the embodiment will be described using the same names and reference numerals, and will be omitted or simplified as appropriate.

Figure 9A:
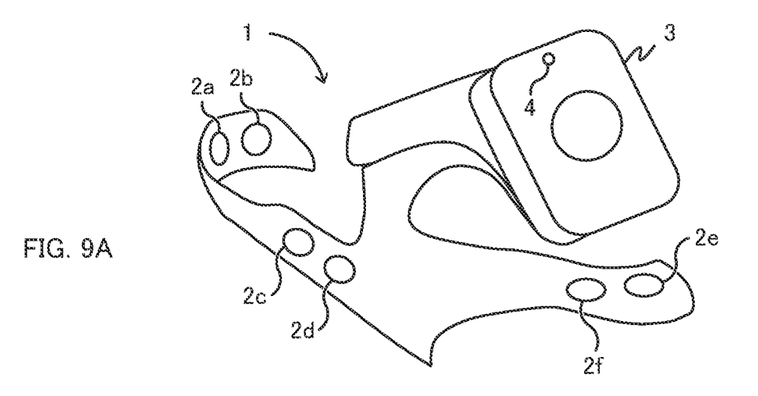
FIGS. 9A to 9C are each a schematic diagram illustrating a guidance support device according to Variation Example 6 of the embodiment.
Figure 9B:
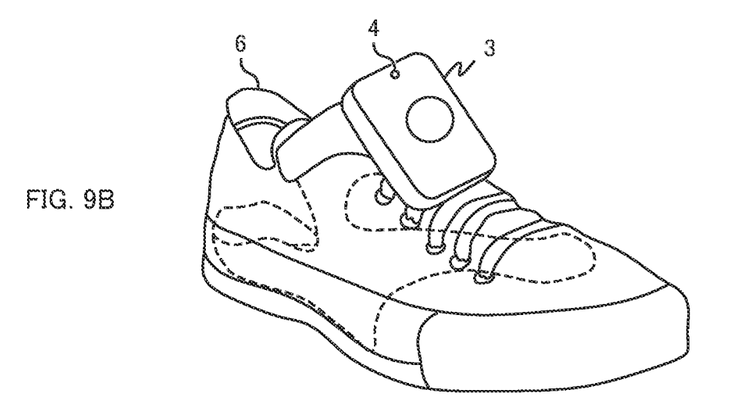
Figure 9C:
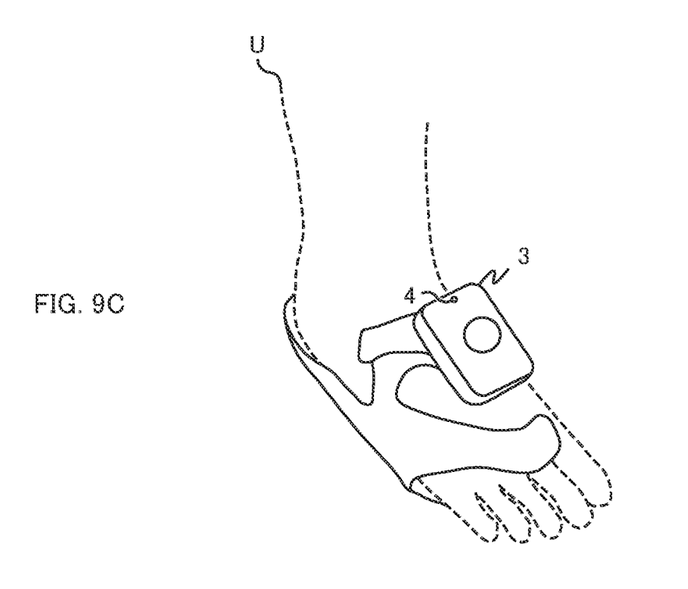

FIGS. 9A to 9C are each a schematic diagram illustrating the guidance support device 1 according to Variation Example 6 of the embodiment. Specifically, FIG. 9A is a schematic diagram showing an external shape of the guidance support device 1 (only for the right foot, while the one for the left foot is not shown) according to Variation Example 6. FIG. 9B is a schematic diagram showing a state in which the guidance support device 1 according to Variation Example 6 is inserted into footwear 6. FIG. 9C is a schematic diagram showing a relationship between the guidance support device 1 according to the Variation Example 6 and the foot of the user U. FIG. 9B shows an example in which the footwear 6 is a sneaker, and a portion of the guidance support device 1 not visible because that portion is inserted in the footwear 6 is indicated by a broken line. In FIG. 9C, the foot of the user U is indicated by a broken line.

The guidance support device 1 according to Variation Example 6 is similar to the insole 1 according to the embodiment in that the guidance support device 1 is used by being inserted in the footwear 6. However, unlike the insole, the guidance support device 1 according to Variation Example 6 is not provided with a member disposed on the sole side of the foot of the user U at the time of use, but instead is formed with a member disposed on the side and the instep side of the foot of the user U. Further, unlike the insole 1 according to the embodiment, in the guidance support device 1 according to Variation Example 6, the processing apparatus 3 is disposed not on the heel but on an upper surface of the instep of the foot or the front of the ankle of the user U at the time of use. In the guidance support device 1 according to Variation Example 6, the distance measuring part 4 is provided on the surface of the processing apparatus 3, and can measure a distance to a distance measurement target that exists in a straight forward direction of the user U when the user U walks.

Similarly to the insole 1 according to the embodiment, in the guidance support device 1 according to Variation Example 6, the vibration generating members 2 are not disposed on the back of the feet of the user U when the guidance support device 1 is worn. Therefore, even if each sensor of the measurement part 5 fails and the guidance support device 1 has a problem in guiding the user U, the user U can continue walking by holding a white cane and acquiring information concerning the ground from the sole as in the related art.

Variation Example 7

Cases where the guidance support device 1 itself detects a failure of each sensor included in the guidance support device 1 were explained above. Alternatively or additionally, the mobile terminal T connected to the guidance support device 1 in a communicable manner may detect the failure of each sensor included in the guidance support device 1. Such a case will be described below.

Figure 10:
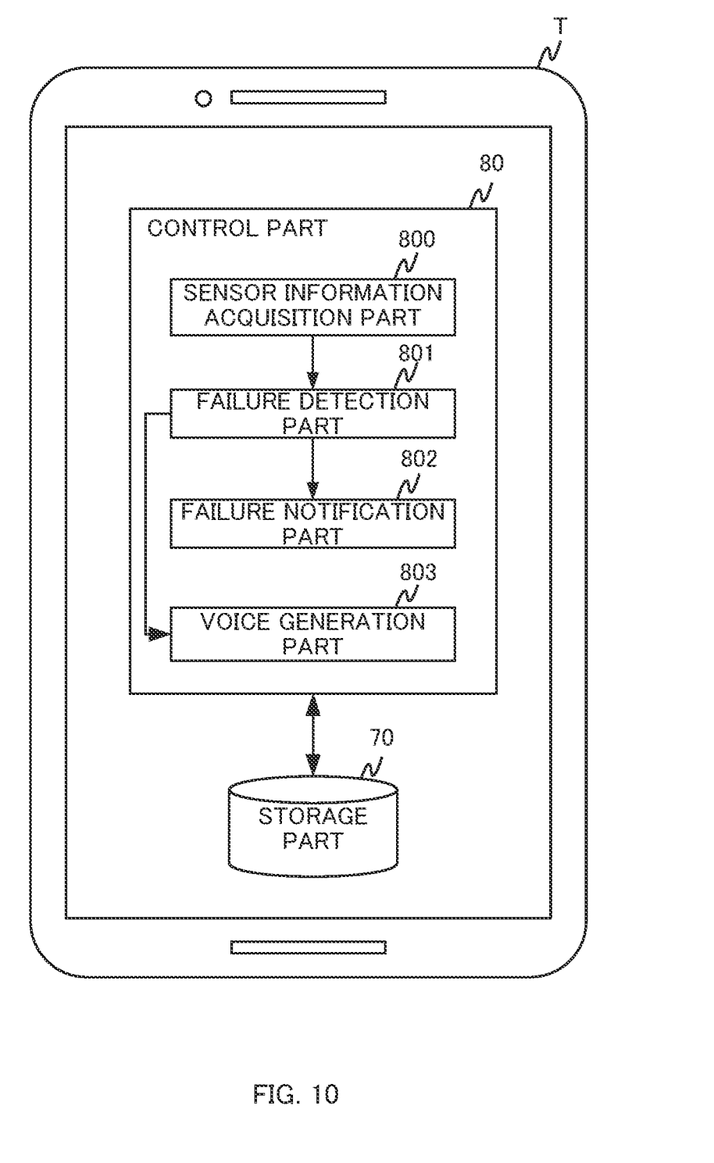
FIG. 10 is a schematic diagram showing a functional configuration of a mobile terminal according to Variation Example 7 of the embodiment.

FIG. 10 is a schematic diagram showing a functional configuration of the mobile terminal T according to Variation Example 7 of the embodiment. The mobile terminal T according to Variation Example 7 has a function equivalent to that of the failure management part 335 according to the above-described embodiment.

As described above, the mobile terminal T is, for example, a known smartphone, and includes a storage part 70 and a control part 80. In FIG. 10, arrows indicate main data flows, and there may be data flows not shown in FIG. 10. In FIG.

7, each functional block indicates a functional unit, not a configuration of a hardware (device) unit. Therefore, the functional blocks shown in FIG. 10 may be implemented in a single device, or may be implemented separately in a plurality of devices.

The storage part 70 is a storage device that stores (i) a ROM which stores a BIOS and the like for a computer that realizes the mobile terminal T, (ii) a RAM which is a work area of the mobile terminal T, (iii) an OS and application programs, and (iv) various types of information to be referenced when executing the application programs. Further, the control part 80 includes a processor such as a CPU or a graphics processing unit (GPU) of the mobile terminal T, and functions as a sensor information acquisition part 800, a failure detection part 801, a failure notification part 802, and a voice generation part 803 by executing the programs stored in the storage part 70.

The sensor information acquisition part 800 acquires the first sensor information which is information acquired by various sensors of the first measurement part, and the second sensor information which is information acquired by various sensors of the second measurement part.

The failure detection part 801 analyzes a difference between the first sensor information and the second sensor information to detect a failure of at least one of the first measurement part or the second measurement part. The failure notification part 802 notifies the first guidance support device and the second guidance support device that the failure has been detected.

In response to a detection of the failure by the failure detection part 801, the failure notification part 802 sends information to a pre-registered external device. When the vibration control part 332 of the first guidance support device and the vibration control part 332 of the second guidance support device receive, from the failure notification part 802, a notification indicating that the failure has been detected, the vibration control part 332 of the first guidance support device and the vibration control part 332 of the second guidance support device respectively continue to vibrate the vibration generating members 2 for a predetermined time (e.g., 10 seconds, time defined for the user U to recognize an instruction to stop) in the combination determined to prompt the user U to stop. By doing this, the guidance support device 1 can prevent the guidance support of the user U from being performed in a state where the failure of the measurement part 5 is suspected. Thereafter, the vibration control part 332 of the first guidance support device and the vibration control part 332 of the second guidance support device respectively stop the vibrations of the vibration generating members 2. By doing this, the guidance support device 1 can prevent the vibration generating members 2 from continuing to vibrate even after the user U stopped.

When the failure detection part 801 detects the failure of at least one of the first measurement part or the second measurement part, the voice generation part 803 causes a speaker (not shown) of the mobile terminal T to generate a warning sound that notifies of the failure. By doing this, the voice generation part 803 can quickly notify the user U that the failure has occurred, even if the user U is visually impaired.

What is claimed is:

1. A guidance support device to be used by being inserted into footwear, the guidance support device comprising:
    a plurality of vibration generating members for generating vibrations at a plurality of positions on an epidermis of a foot of a user who uses the guidance support device;
    a position acquisition part that acquires a current position;
    a route acquisition part that acquires a route from the current position to a destination; and
    a vibration control part that, on condition that a route pattern at a current position on the route fits any one of a plurality of predetermined route patterns, vibrates the vibration generating members in a combination corresponding to the route pattern at the current position, each of the route patterns showing a type of change in motion that should be taken by the user in order to guide the user to the destination, wherein
    the guidance support device is a first guidance support device used by being worn on one of the feet of the user, and
    the guidance support device further comprises:
    a sensor information acquisition part that acquires first sensor information, which is information acquired by a sensor of a measurement part included in the first guidance support device, and second sensor information, which is information acquired by a sensor of a measurement part included in a second guidance support device used by being worn on an other foot of the user;
    a failure detection part that analyzes a difference between the first sensor information and the second sensor information and detects a failure of at least one of the measurement part included in the first guidance support device or the measurement part included in the second guidance support device; and
    a failure notification part that notifies the second guidance support device that the failure has been detected.

2. The guidance support device according to claim 1, wherein the position acquisition part comprises:
    a positioning position acquisition part that acquires a positioning position on the basis of navigation signals received from a navigation satellite;
    a map acquisition part that acquires map information including the route;
    a position estimation part that estimates a relative position based on a base point position that is in the map information; and
    a position correction part that calculates the current position by correcting the positioning position using the relative position,
    the guidance support device further comprises a distance measuring part that measures a distance to an object around the footwear, and
    the position estimation part updates the base point position on the basis of information concerning a distance measurement target included in the map information and the distance measured by the distance measuring part.

3. The guidance support device according to claim 2, wherein the vibration control part vibrates the vibration generating members in a combination determined to prompt the user to stop, when the distance measuring part cannot detect a distance measurement target.

4. The guidance support device according to claim 2, further comprising:
    a destination accepting part that accepts setting of the destination; and
    a distance measurement target acquisition part that acquires, by referencing a distance measurement target database that stores (i) a plurality of segmented regions set in advance in the map information and (ii) information concerning the distance measurement target determined for each segmented region in association with each other, information concerning a distance measurement target associated with a segmented region in which the destination is included.

5. The guidance support device according to claim 2, wherein the distance measuring part is provided such that the distance measuring part is positioned at the heel of the user.

6. The guidance support device according to claim 1, wherein the failure notification part notifies a notification destination registered in advance via a mobile terminal that can communicate with the guidance support device in response to the failure being detected.

7. The guidance support device according to claim 1, wherein the vibration control part stops the vibrations of the vibration generating members after having the vibration generating members continue to vibrate for a predetermined time in a combination determined to prompt the user to stop, when the failure is detected.

8. Footwear which is a pair of footwear to be worn respectively on the feet of a user, the footwear respectively comprising:
   a plurality of vibration generating members for generating vibrations at a plurality of positions on an epidermis of one of the feet of the user;
   a position acquisition part that acquires a current position;
   a route acquisition part that acquires a route from the current position to a destination;
   a vibration control part that, on condition that a route pattern included in the route at the current position fits any one of a plurality of predetermined route patterns, vibrates the vibration generating members in a combination corresponding to the route pattern at the current position, each of the route patterns showing a type of change in motion that should be taken by the user in order to guide the user to the destination;
   a sensor information acquisition part that acquires first sensor information, which is information acquired by a sensor of a measurement part included in the footwear used by being worn on one of the feet of the user, and second sensor information, which is information acquired by a sensor of a measurement part included in footwear used by being worn on the other foot of the user;
   a failure detection part that analyzes a difference between the first sensor information and the second sensor information and detects a failure of at least one of the measurement part included in the footwear worn on one of the feet of the user or the measurement part included in the footwear worn on the other foot of the user; and
   a failure notification part that notifies the footwear worn on the other foot of the user that the failure has been detected.

* * * * *